United States Patent
Iwase et al.

(10) Patent No.: US 10,335,551 B2
(45) Date of Patent: Jul. 2, 2019

(54) NEEDLE ASSEMBLY AND DRUG INJECTION DEVICE

(71) Applicant: TERUMO KABUSHIKI KAISHA, Tokyo (JP)

(72) Inventors: Yoichiro Iwase, Kanagawa (JP); Kazunori Koiwai, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 74 days.

(21) Appl. No.: 15/470,831

(22) Filed: Mar. 27, 2017

(65) Prior Publication Data
US 2017/0197035 A1 Jul. 13, 2017

Related U.S. Application Data

(63) Continuation of application No. PCT/JP2015/076120, filed on Sep. 15, 2015.

(30) Foreign Application Priority Data

Sep. 29, 2014 (JP) ................................ 2014-198435

(51) Int. Cl.
*A61M 5/31* (2006.01)
*A61M 5/32* (2006.01)
(Continued)

(52) U.S. Cl.
CPC .......... *A61M 5/3134* (2013.01); *A61M 5/158* (2013.01); *A61M 5/178* (2013.01);
(Continued)

(58) Field of Classification Search
CPC .... A61M 5/3134; A61M 5/158; A61M 5/178; A61M 5/344; A61M 5/346; A61M 5/347
(Continued)

(56) References Cited

U.S. PATENT DOCUMENTS 2,864,366 A * 12/1958 Miskel ................... A61M 5/24
604/190
5,041,097 A 8/1991 Johnson
(Continued)

FOREIGN PATENT DOCUMENTS

EP 2703028 A1 3/2014
JP 2011-212185 A 10/2011
(Continued)

OTHER PUBLICATIONS

International Search Reoort issued in International Patent Apoplicaiton No. PCT/JP2015/076120 dated Dec. 22, 2015.
Extended European Search Report dated Aug. 21, 2018 in corresponding application No. 15845873.

*Primary Examiner* — Phillip A Gray
(74) *Attorney, Agent, or Firm* — Foley & Lardner LLP

(57) ABSTRACT

A needle assembly includes: a retaining portion; and an elastic member that includes a close contact portion that closely contacts and retains the needle tube such that the needle tube protrudes toward a fitting opening, and a deformation portion that extends from the close contact portion toward the fitting opening and is configured to deform when the drug ejection portion comes into contact with the elastic member, and which is provided in a fitting portion. Further, the length of the deformation portion is in a range of 35% or more and 50% or less with respect to the length of the elastic member, and the length of a portion of the needle tube which protrudes from the close contact portion toward the fitting portion is in a range of 45% or more and 245% or less with respect to the deformation portion.

8 Claims, 7 Drawing Sheets

(51) Int. Cl.
*A61M 5/34* (2006.01)
*A61M 5/158* (2006.01)
*A61M 5/178* (2006.01)

(52) U.S. Cl.
CPC ............ *A61M 5/344* (2013.01); *A61M 5/346* (2013.01); *A61M 5/347* (2013.01); *A61M 2005/3103* (2013.01); *A61M 2005/3131* (2013.01); *A61M 2005/3142* (2013.01); *A61M 2005/3206* (2013.01)

(58) Field of Classification Search
USPC ........................................................ 604/240
See application file for complete search history.

(56) References Cited

U.S. PATENT DOCUMENTS

| | | | |
|---|---|---|---|
| 5,330,435 A * | 7/1994 | Vaillancourt | ....... A61M 39/045 241/149 |
| 2013/0079729 A1 | 3/2013 | Yokota et al. | |

FOREIGN PATENT DOCUMENTS

| | | |
|---|---|---|
| JP | 2012-517326 A | 8/2012 |
| WO | WO-2010/093791 A1 | 8/2010 |
| WO | WO-2012-157313 A1 | 11/2012 |
| WO | WO-2012-160852 A1 | 11/2012 |

* cited by examiner

NEEDLE ASSEMBLY AND DRUG INJECTION DEVICE

CROSS-REFERENCE TO RELATED APPLICATIONS

The present application is a bypass continuation of PCT Application No. PCT/JP2015/076120, filed on Sep. 15, 2015, which claims priority to Japanese Application No. 2014-198435, filed on Sep. 29, 2014, the disclosures of which are hereby incorporated by reference in their entireties.

BACKGROUND

The present disclosure relates to a needle assembly that is fitted to a drug ejection portion of a drug container such as an injection syringe to use, and a drug injection device that includes such a needle assembly.

In some drug injection devices, a syringe that contains an injection drug, and a needle assembly that includes a needle are separately formed, and the needle assembly is attached to a drug ejection portion at a cylindrical tip of the syringe and is used for injection. See, e.g., JP 2011-212185 A.

A needle assembly is generally attached to a drug ejection portion by taper fitting. More specifically, the drug ejection portion is formed in a male tapered shape (truncated conical shape) whose outer diameter continuously becomes smaller toward a distal end. The needle assembly is provided with a fitting portion including a cylindrical hole, and this fitting portion is formed in a female tapered shape (truncated conical shape) that has a size matching the drug ejection portion and whose inner diameter continuously becomes smaller from an opening including the cylindrical hole. The male tapered shape and the female tapered shape are formed at the same taper rate. By pressuring a drug ejection tube and pushing the fitting portion, surfaces of the tapered shapes press against each other and are fixed in liquid-tight manner.

SUMMARY

In a drug injection device in which a drug container such as a syringe and a needle assembly are connected by taper fitting, a side of a retained needle tube of the needle assembly inserted in a drug ejection portion is inserted in an elastic member. Thus, the elastic member and the needle assembly are retained in a liquid-tight manner, so that it is possible to prevent leakage of a drug toward a needle tip. Further, when the drug ejection portion is fitted to the fitting portion of the needle assembly, a distal end of the drug ejection portion comes into contact with an end surface of the elastic member. Thus, it is possible to reduce a dead volume due to a difference in a connection force of a user for connecting an injection syringe to a drug injection device or a difference in a fitting depth caused by a dimensional error between the drug injection device and the injection syringe.

However, the elastic member deforms when the drug ejection portion comes into contact with the elastic member. Therefore, it is possible to reduce a dead volume when the drug ejection portion comes into contact with the elastic member and the elastic member deforms by adjusting a length of a needle tube inserted in the elastic member. However, the deformed elastic member can block a proximal end of the needle tube at a side of a drug ejection portion, and a liquid passing failure can occur. Further, when the drug ejection portion comes into contact with the elastic member and the elastic member deforms to a greater extent, the liquid passing failure is more likely to occur.

It is therefore an object of the present disclosure to provide a needle assembly that prevents a liquid passing failure, and a drug injection device which includes such a needle assembly.

A needle assembly according to one embodiment of the present invention is a needle assembly that is connectable to a drug container such as a syringe including a drug ejection portion having a male tapered shape with an outer diameter that becomes smaller toward a distal end. The needle assembly includes a needle tube that includes at a distal end a needle tip configured to puncture skin; a retaining portion that includes a fitting portion including a fitting opening in which the drug ejection portion is insertable, and formed in a female tapered shape, and which retains the needle tube in a state where a proximal end of the needle tube protrudes toward the fitting opening; and an elastic member that is located in the fitting portion, and includes a close contact portion that closely contacts and retains a proximal end side of the needle tube protruding toward the fitting opening, and a deformation portion that extends from the close contact portion toward the fitting opening and deforms when the drug ejection portion comes into contact with the elastic member, and in which a length of the deformation portion is in a range of 35% or more and 50% or less with respect to a length of the elastic member, and a length of the needle tube which protrudes from the close contact portion toward the fitting portion is in a range of 45% or more and 245% or less with respect to the deformation portion.

Further, a drug injection device according to one embodiment of the present invention includes: a drug container such as a syringe that includes a drug ejection portion of a cylindrical shape formed in a male tapered shape whose outer diameter becomes smaller toward a distal end; and the above-described needle assembly.

According to certain embodiments of the present invention, it is possible to provide a needle assembly which prevents liquid passing failure, and a drug injection device that includes such a needle assembly.

DETAILED DESCRIPTION

An example of a needle assembly and a drug injection device according to an embodiment of the present invention will be described with reference to the drawings. The present invention is not limited to the following example. This description will be described in the following order.

1. Configurations of Needle Assembly and Drug Injection Device

2. Method for Assembling Drug Injection Device

<1. Configurations of Needle Assembly and Drug Injection Device>

[Drug Injection Device]

Figure 1:
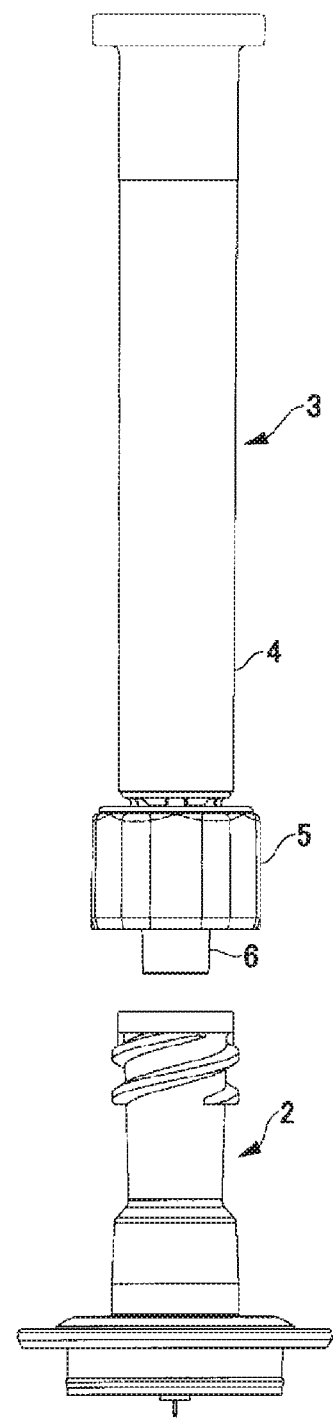
FIG. 1 is an exploded side view of a drug injection device according to one embodiment of the present invention.
Figure 2:
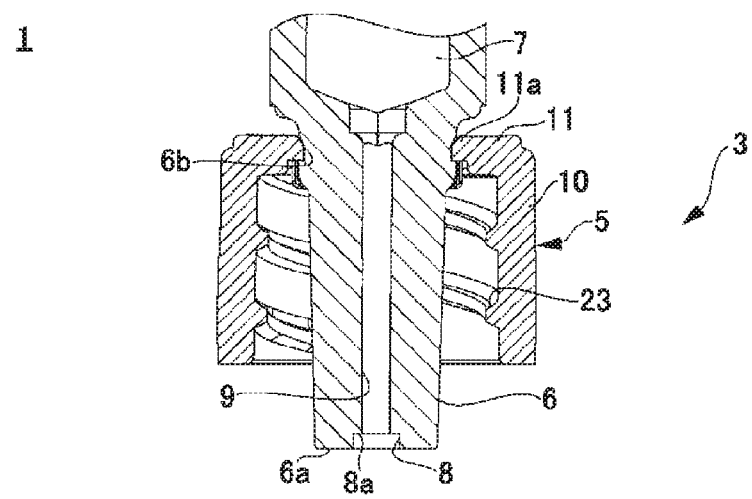
FIG. 2 is a sectional view illustrating enlarged main portions of the drug injection device illustrated in FIG. 1.
Figure 2:
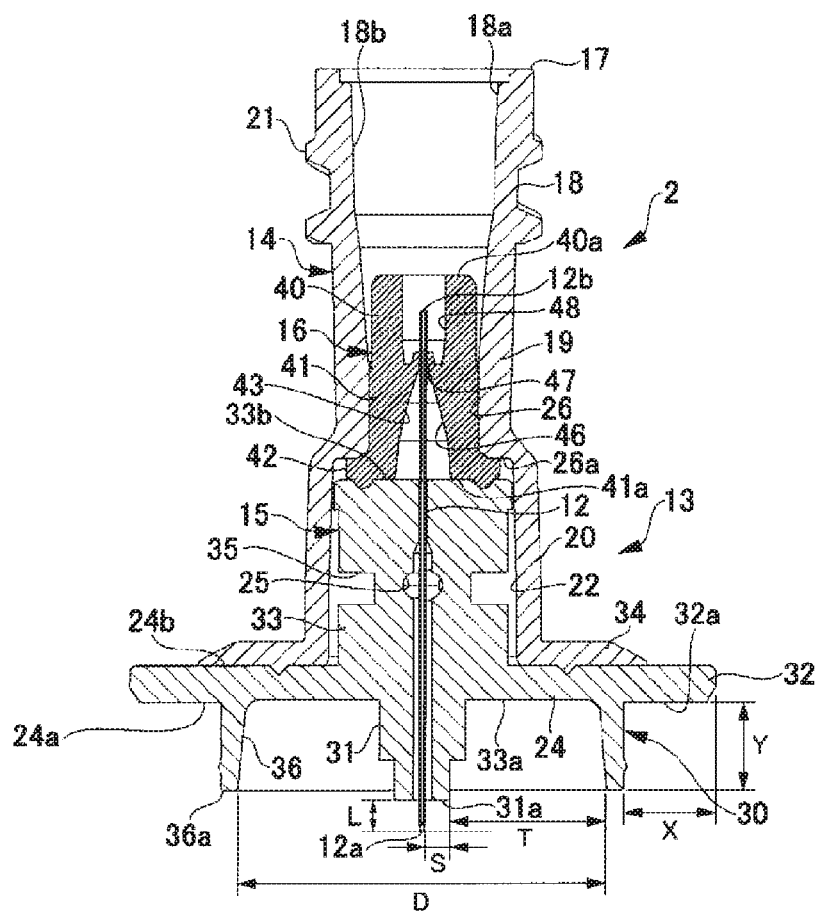

FIG. 1 is an exploded side view of a drug injection device according to one embodiment of the present invention. FIG. 2 is a sectional view illustrating enlarged main portions of the drug injection device illustrated in FIG. 1. A drug injection device 1 is used to puncture a skin surface by a needle tip and inject a drug. In the present embodiment, the drug injection device 1 is for intradermal injection, for injecting a drug in a skin upper layer portion.

In this regard, the skin is composed of three portions of epidermis, dermis and subcutaneous tissues. The epidermis is a layer which is approximately 50 to 200 μm from a skin surface, and the dermis is a layer which is approximately 1.5 to 3.5 mm from the epidermis. An influenza vaccine is generally administered by subcutaneous administration or intramuscular administration, and therefore is administered to a lower layer portion of the skin or a deeper portion than this lower layer portion.

Generally, administering an influenza vaccine to a target site of a skin upper layer portion including multiple immunocompetent cells to decrease a vaccine dose is studied. In this regard, the skin upper layer portion refers to the epidermis and the dermis of the skin. The drug injection device 1 according to the present embodiment is the drug injection device 1 for intradermal injection at a target site of such a skin upper layer portion.

As illustrated in FIG. 1, the drug injection device 1 according to the present embodiment includes a needle assembly 2, and a syringe (drug container) 3 to which the needle assembly 2 is detachably attached. Although not illustrated, a plunger for pushing out a drug is inserted in the syringe 3. Further, an end portion of the syringe 3 connected to the needle assembly 2 is provided with a lock mechanism 5.

[Syringe]

The syringe 3 includes a syringe main body 4, a drug ejection portion 6 which continues to this syringe main body 4, and the lock mechanism 5 which is provided at an outer circumference of the drug ejection portion 6. The syringe main body 4 is composed of a cylindrical member and, as illustrated in FIG. 2, an interior of the cylinder is a drug containing portion 7 which contains a drug. The drug ejection portion 6 is provided at one end of the syringe main body 4 in an axial direction, and is composed of a cylindrical member which is connected to the drug containing portion 7.

The drug ejection portion 6 is formed in a male tapered shape whose outer diameter is smaller than the syringe main body 4 and becomes smaller toward a distal end. In this regard, a taper rate is expressed in fraction such as A/100 or in percentage such as A % when, for example, a diameter becomes thinner by A mm per 100 mm in length. In the present embodiment, the male tapered shape forming the drug ejection portion 6 is formed at N/100. N is a positive number. More specifically, the male tapered shape is formed at N=6 which is also referred to as a luer taper in accordance with ISO594-1 or ISO594-2.

Further, as illustrated in FIG. 2, an expanded portion 8 formed by expanding a diameter of a cylindrical hole 9 is formed at a distal end side of the cylindrical hole 9 of the drug ejection portion 6. The depth of this expanded portion 8, i.e., the length from a distal end 6a of the drug ejection portion 6 to an end surface 8a of the expanded portion 8 in an axial direction is approximately 0.4 mm to 0.6 mm. When injection is performed for the skin upper layer portion, a dose is approximately 0.1 to 0.3 mL and is less than those of subcutaneous injection and intramuscular injection. Therefore, it is necessary to reduce a dead volume of the syringe main body 4 to prevent a drug from being wasted. Hence, the drug ejection portion 6 is generally thicker than common syringes, and is concerned to bend a core pin of a mold during molding. The expanded portion 8 is formed to prevent the core pin from being bent.

A flat surface orthogonal to an axial center direction of the distal end 6a is formed at the distal end 6a of the drug ejection portion 6, and an outer shape of the flat surface, i.e., a distal end outer rim of the drug ejection portion 6 is formed in a circular shape. The flat surface of the distal end 6a of the drug ejection portion 6 and a side surface (a side surface of the tapered shape) of the drug ejection portion 6 are connected at the distal end outer rim of the drug ejection portion 6. The flat surface of the distal end 6a of this drug ejection portion 6 comes into contact with an end surface of an elastic member 16 of the needle assembly 2 in a liquid-tight manner when attached to the needle assembly 2. Further, a recessed portion 6b in which fitting claws 11a of the lock mechanism 5 described below are formed in an outer circumference surface of an end portion (referred to as a proximal end below) of the drug ejection portion 6 at a side of the syringe main body 4.

For example, the syringe main body 4 and the drug ejection portion 6 are formed of a synthetic resin (plastic). A material of this synthetic resin is, for example, polycarbonate, polypropylene, polyethylene, cyclo-olefin polymer or the like.

The lock mechanism 5 is provided to cover the outer circumference surface of the drug ejection portion 6, and includes a lock main body portion 10 which is described below and is fixed to the needle assembly 2, and a lock mechanism fixing portion 11 which fixes the lock main body portion 10 to the drug ejection portion 6.

The lock main body portion 10 is composed of a cylindrical member which coaxially surrounds the drug ejection portion 6. The lock main body portion 10 has an inner circumference of a circular shape and an outer circumference of a hexagonal shape to allow a user to easily turn the lock main body portion 10. A female screw portion 23 is formed in an inner circumference surface of the lock main body portion 10. This female screw portion 23 is formed so as to allow the male screw portion 21 formed in a fitting portion 18 of the needle assembly 2 described below to be screwed therein. In the present embodiment, the female screw portion 23 is formed as a thread groove of a double helical shape.

The lock mechanism fixing portion 11 is integrally formed with the lock main body portion 10 at an end portion of the lock main body portion 10 at the side of the syringe main body 4. The lock mechanism fixing portion 11 is composed of a hollow disk-shaped member formed to reduce an inner diameter of the lock main body portion 10. An inner circumference surface of the lock mechanism fixing portion 11 facing the drug ejection portion 6 is provided with the fitting claws 11a which fit to the drug ejection portion 6. An inner diameter of the lock mechanism fixing portion 11 is formed slightly larger than the outer diameter of the drug ejection portion 6. The fitting claws 11a are formed protruding in a radial direction from the inner circumference surface of the lock mechanism fixing portion 11 facing the drug ejection portion 6, and a plurality of fitting claws 11a are formed on the inner circumference surface of the lock mechanism fixing portion 11 at equal intervals.

The lock mechanism 5 employing such a configuration is composed of a member different from the syringe 3, and is fixed by fitting the fitting claws 11a to the recessed portion 6b formed in an outer circumference surface of the proximal end of the drug ejection portion 6. The lock mechanism 5 can be formed by using the same material as that of the syringe main body 4 and the drug ejection portion 6.

[Needle Assembly]

Figure 4:
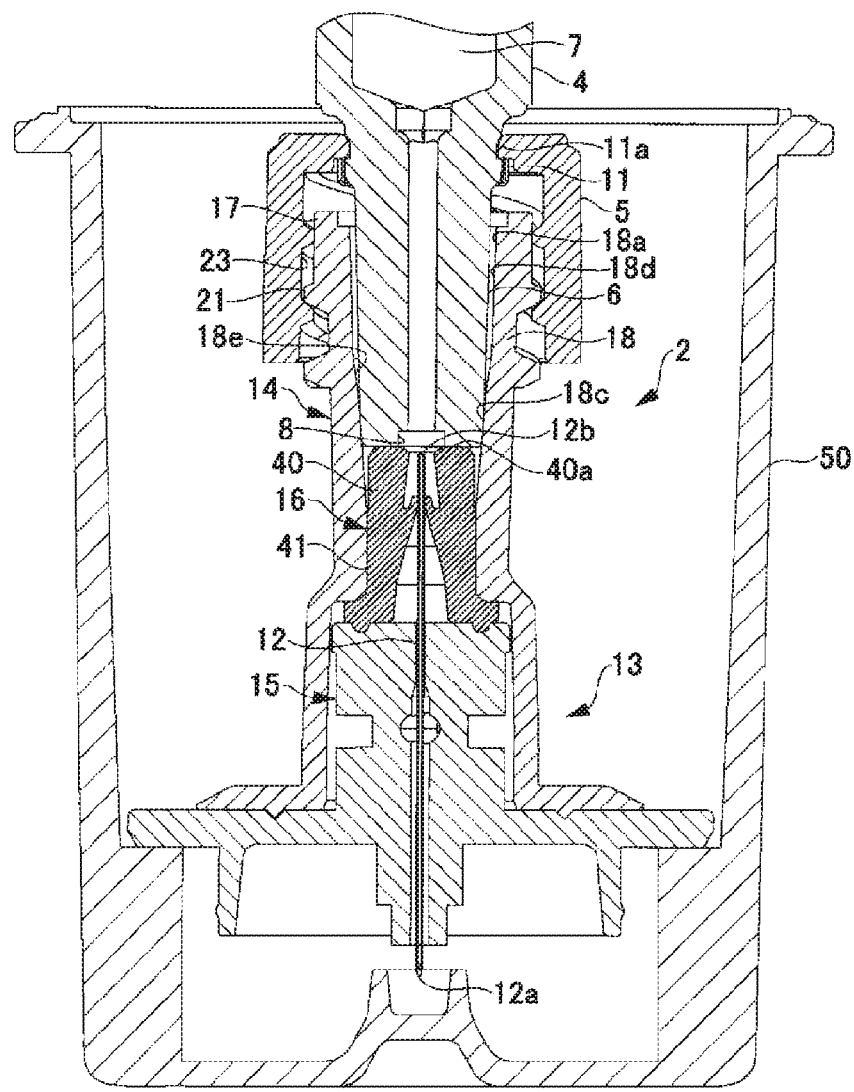
FIG. 4 is a view (part 1) illustrating how a drug ejection portion of a syringe is fitted to a needle assembly to assemble the drug injection device.

The needle assembly 2 includes a needle tube 12 and a needle hub 13 that retains the needle tube 12. Further, before the needle assembly 2 is connected with the syringe 3, the needle assembly 2 is detachably attached to a cap 50 as illustrated in FIG. 4.

For the needle tube 12, a needle tube of a 26 to 33 gauge size (outer diameter is 0.2 to 0.45 mm) according to medical needle tube standards of ISO (ISO9626:1991/Amd.1:2001 (E)) is used, and, more preferably, a needle tube of a 30 to 33 gauge size is used.

A needle tip 12a that includes a blade surface is formed at a distal end of the needle tube 12. The other end of the needle tube 12, which is at a side opposite to the needle tip 12a, will be referred to as a "proximal end 12b" below. The length of the needle tube 12 on the blade surface in the axial direction (such a length will be referred to as a "bevel length" below) needs to be 1.4 mm (adult) or less which is the least thickness of the skin upper layer portion described below, and needs to be approximately 0.5 mm or more which is the bevel length in case where a short bevel is formed in a 33-gauge needle tube. That is, the bevel length is preferably set to a range of 0.5 to 1.4 mm.

Further, the bevel length is more preferably 0.9 mm (child) or less which is the least thickness of the skin upper layer portion, i.e., a bevel length B is more preferably in a range of 0.5 to 0.9mm. In this regard, the short bevel refers to a blade surface that forms an 18° to 25° angle with respect to a longitudinal direction of a needle, which is generally used for a needle.

A material of the needle tube 12 is, for example, stainless steel yet is not limited to this. Other metals such as aluminum, aluminum alloy, titanium and titanium alloy can be used for this material. Further, for the needle tube 12, not only a straight needle but also a tapered needle which is at least partially tapered can be used. The tapered needle needs to have a base end portion which has a larger diameter than a needle tip end portion, and an intermediate portion which adopts a tapered structure. Further, a sectional shape of the needle tube 12 may be not only a circular shape but also a polygonal shape such as a triangular shape.

The needle hub 13 includes a first member 14 which is provided with the fitting portion 18 to which the drug ejection portion 6 of the syringe 3 is fitted, a second member 15 (a retaining portion according to the present invention) which retains the needle tube 12, and the elastic member 16 which is sandwiched between the drug ejection portion 6 and the second member 15 during assembly of the drug injection device 1. In the present embodiment, the first member 14 and the second member 15 forming the needle hub 13 are formed by using different members yet may be integrally formed.

[First Member]

The first member 14 is entirely formed in a nearly cylindrical shape. In the first member 14, a limiting portion 17 which limits a force to be applied to the lock mechanism 5, the fitting portion 18 to which the drug ejection portion 6 is fitted, an intermediate portion 19 in which the elastic member 16 is inserted and an insertion portion 20 in which the second member 15 is inserted are formed in order from a side at which the drug ejection portion 6 is inserted.

A cylindrical hole 18b of the fitting portion 18 is set to a size matching the drug ejection portion 6 of the syringe 3, and an opening end at one end side is a fitting opening 18a fitted to the drug ejection portion 6. Further, the diameter of the fitting portion 18 becomes continuously smaller from an end portion of the fitting opening 18a toward the insertion portion 20.

Figure 3:
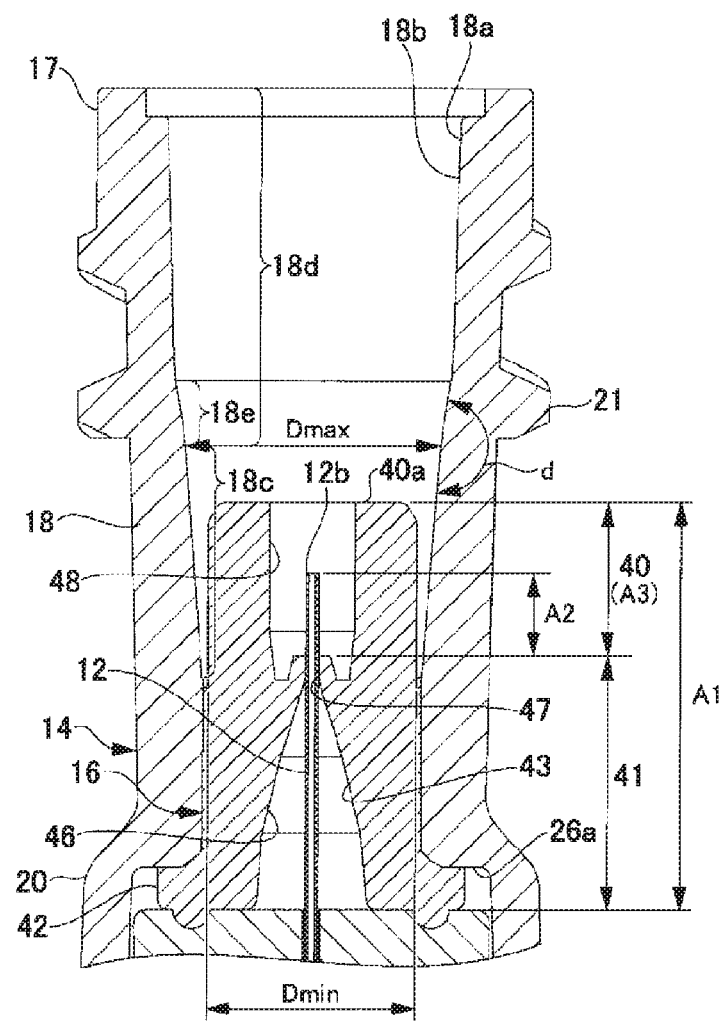
FIG. 3 is an enlarged sectional view of a fitting portion of a first member.

FIG. 3 is an enlarged sectional view of the fitting portion 18 of the first member 14. Configurations of the fitting portion 18 and the limiting portion 17 will be described in more detail with reference to FIG. 3. The fitting portion 18 includes a fitting wall 18c, which fits to the drug ejection portion 6 in an inner wall of the cylindrical hole 18b. As illustrated in FIG. 3, the fitting portion 18 preferably includes a guide wall 18d in the inner wall of the cylindrical hole 18b at a side of the fitting opening 18a. The fitting wall 18c is formed in such a female tapered shape that an inner diameter of the cylindrical hole 18b becomes continuously smaller from the side of the fitting opening 18a toward a side of the insertion portion 20. This tapered shape is formed with a taper rate of M>100 where M>N holds. M is a positive number. In this example, M takes a value larger than 6 to match the taper rate of N/100 (N=6 in the present embodiment) for the outer diameter of the drug ejection portion 6.

The fitting wall 18c is formed such that the inner diameter of the cylindrical hole 18b can be fitted to the drug ejection portion 6 of the syringe 3. When K represents the diameter of the distal end of the drug ejection portion 6, Dmax represents the diameter (maximum diameter) of the fitting wall 18c at the side of the fitting opening 18a, and Dmin represents the diameter (minimum diameter) of the fitting wall 18c at the side of the insertion portion 20, the cylindrical hole 18b corresponding to the fitting wall 18c is formed to provide a relationship of Dmax>K>Dmin. The distal end of the fitted drug ejection portion 6 is positioned at the position slightly closer to the side of the insertion portion 20 than the position at which the diameter of the cylindrical hole 18b is K.

The guide wall 18d is formed by expanding the inner diameter of the cylindrical hole 18b at the side of the fitting opening 18a. This guide wall 18d is preferably formed by expanding the inner diameter of the cylindrical hole 18b at the side of the fitting opening 18a compared to a case where the entire cylindrical hole 18b is formed by the fitting wall 18c at the tapered rate of M/100. The guide wall 18d is preferably formed in such a tapered shape that the inner diameter of the cylindrical hole 18b becomes smaller from the side of the fitting opening 18a toward the side of the insertion portion 20.

The length of the guide wall 18d in the axial line direction is approximately 0.5 L to 2 L when, for example, L represents the length of the fitting wall 18c in the axial line direction.

Further, the guide wall 18d and the fitting wall 18c are not preferably connected in a stepwise shape to prevent leakage of a drug solution due to damage on the distal end of the drug ejection portion 6. That is, as illustrated in FIG. 3, an angle d at which the connection wall 18e of a tapered shape whose diameter at the side of the insertion portion 20 becomes small or the connection wall 18e which is formed by curves connects the guide wall 18d and the fitting wall 18c is preferably formed at an obtuse angle ($90° < d < 180°$) and is more preferably formed at $120° \leq d \leq 180°$.

A second screw portion (referred to as a male screw portion 21) to which the female screw portion 23 of the lock mechanism 5 is screwed is formed on an outer circumference surface of the fitting portion 18. In the present embodiment, the male screw portion 21 is formed as a thread of a double helical shape. In this regard, the male screw portion 21 may be a screw of a single helical shape.

The limiting portion 17 is formed at the end portion of the fitting opening 18a of the fitting portion 18, and includes a cylindrical member including a cylindrical hole continuing to the cylindrical hole 18b of the fitting portion 18. An outer circumference surface of the limiting portion 17 and an outer circumference surface of the fitting portion 18 are formed as a continuous surface, and an outer diameter of the continuous surface is formed to be substantially the same as an outer diameter of the fitting portion 18 at the side of the fitting opening 18a. Further, an inner circumference surface of the limiting portion 17 and an inner circumference surface of the fitting portion 18 are formed as a continuous surface, and an inner diameter of the continuous surface is formed to be slightly larger than an inner diameter of the fitting opening 18a of the fitting portion 18.

Furthermore, the length of the limiting portion 17 in the axial direction is set to come into contact with the lock mechanism fixing portion 11 of the lock mechanism 5 during assembly of the drug injection device 1. The limiting portion 17 is a portion provided to limit a pushing force applied to the lock mechanism 5 to push and assemble the drug ejection portion 6 of the syringe 3 to the fitting portion 18 of the needle assembly 2. A function of this limiting portion 17 will be described in detail below.

Next, a configuration of the insertion portion 20 will be described with reference back to FIG. 2. A cylindrical hole 22 of the insertion portion 20 is set to a size matching a base portion 33 of the second member 15. The insertion portion 20 is provided with a fixing piece 34 which is connected to a connection piece 24 of the second member 15 described below. This fixing piece 34 is formed as a flange of a ring shape which continues to a distal end of the insertion portion 20 and protrudes in a radially outer direction. A planar surface 24b of the connection piece 24 provided to the second member 15 comes into contact with and is fixed to the fixing piece 34. A method for fixing the fixing piece 34 and the connection piece 24 includes, for example, an adhesive, ultrasonic welding, laser welding, a fixing screw and the like.

The intermediate portion 19 is formed between the insertion portion 20 and the fitting portion 18, and is formed as a cylindrical hole 26 whose diameter is smaller than a cylindrical hole 22 of the insertion portion 20. A step surface at a boundary between the cylindrical hole 22 forming the insertion portion 20 and the cylindrical hole 26 forming the intermediate portion 19 is an engagement portion 26a with which the elastic member 16 engages. A flange portion 42 of the elastic member 16 described below engages with this engagement portion 26a.

[Second Member]

The second member 15 is provided with a skin contact portion 30, which faces and/or contacts a skin. The skin contact portion 30 is disposed to cover surroundings of the needle tube 12 when the needle tube 12 is attached to the second member 15. This skin contact portion 30 includes a base portion 33 of a nearly columnar shape, an adjusting portion 31, a stable portion 36 and a guide portion 32.

The base portion 33 includes end surfaces 33a and 33b vertical to the axial direction. The adjusting portion 31 is formed at a center portion of the end surface 33a at one end side of the base portion 33 in the axial direction, and includes a protrusion portion of a columnar shape protruding in the axial direction of the base portion 33. An axial center of this adjusting portion 31 matches with an axial center of the base portion 33.

A through-hole 25 through which the needle tube 12 penetrates is formed at the axial centers of the base portion 33 and the adjusting portion 31. Further, an injection hole 35 through which an adhesive (not illustrated) is injected in the through-hole 25 is formed in the base portion 33. This injection hole 35 is opened in an outer circumference surface of the base portion 33, and continues to the through-hole 25 nearly orthogonally to the through-hole 25 although not illustrated in FIG. 2. That is, the adhesive injected to the through-hole 25 through the injection hole 35 fixes the needle tube 12 to the base portion 33.

The proximal end 12b of the needle tube 12 protrudes from an end surface 33b which is the other end of the base portion 33 in the axial direction. The base portion 33 is inserted in the first member 14 from a side of the end surface 33b, and a side of the proximal end 12b of the needle tube 12 is inserted in an insertion hole 43 of the elastic member 16 described below. Further, the end surface 33b of the base portion 33 is placed in contact with an end surface 41a of the elastic member 16 described below.

Furthermore, the connection piece 24 is provided on an outer circumference surface of the base portion 33. This connection piece 24 is formed as a flange of a ring shape protruding to an outside of a radial direction of the base portion 33, and includes planar surfaces 24a and 24b opposing in the axial direction of the base portion 33. The planar surface 24b of the connection piece 24 is connected with the first member 14. Further, a distal end portion of the connection piece 24 is the guide portion 32. This guide portion 32 will be described in detail below.

An end surface of the adjusting portion 31 is a needle protrusion surface 31a from which a side of the needle tip 12a of the needle tube 12 protrudes. The needle protrusion surface 31a is formed as a planar surface orthogonal to the axial direction of the needle tube 12. This needle protrusion surface 31a comes into contact with a skin surface and defines a puncturing depth of the needle tube 12 when the needle tube 12 punctures a skin upper layer portion. That is, the puncturing depth of the needle tube 12 with respect to the skin upper layer portion is determined according to a protrusion length of the needle tube 12 (referred to as a "protrusion length L" below) from the needle protrusion surface 31a.

The thickness of the skin upper layer portion corresponds to the depth from the skin surface to a dermis layer, and is roughly in a range of 0.5 to 3.0 mm. Hence, the protrusion length L of the needle tube 12 can be set to a range of 0.5 to 3.0 mm.

A vaccine is generally administered to an upper arm portion yet is preferably administered to a shoulder proximity portion of a thick skin and a deltoid portion when administration of the vaccine to a skin upper layer portion is taken into account. Hence, the thicknesses of the skin upper layer of deltoids of 19 children and 31 adults were measured. This measurement was conducted to capture images of the skin upper layer portions of a high ultrasonic reflectance by using an ultrasonic measuring device (NP60R-UBM small animal high resolution echo device manufactured by Nepa Gene Co., Ltd). In this regard, measurement values were provided in a lognormal distribution, and therefore a range of MEAN±2SD was calculated by geometric mean.

A measurement result showed that the thicknesses of the skin upper layer portions of the deltoids of the children were 0.9 to 1.6 mm. Further, the thicknesses of the skin upper layer portions of the deltoids of the adults were 1.4 to 2.6 mm at distal portions, 1.4 to 2.5 mm at center portions and 1.5 to 2.5 mm at proximal portions. In view of the above, it was confirmed that the thicknesses of the skin upper layer portions of the deltoids were 0.9 mm or more in case of the children and 1.4 mm or more in case of the adults. Hence, the protrusion length L of the needle tube 12 is preferably set to the range of 0.9 to 1.4 mm for injection with respect to the skin upper layer portion of the deltoid.

By setting the protrusion length L in this way, it is possible to reliably position the blade surface of the needle tip 12a at the skin upper layer portion. As a result, even when a needle hole (drug outlet) opened in the blade surface is any position on the blade surface, the needle hole can be positioned at the skin upper layer portion. In this regard, even when the drug outlet is positioned at the skin upper layer portion, if the needle tip 12a deeply punctures the skin upper layer portion, a drug solution leaks below the skin from between a side surface of an end portion of the needle tip 12a and a skin cut open. Therefore, it is important to reliably place the blade surface at the skin upper layer portion.

In this regard, in case of use for administration to the skin upper layer portion, a needle tube thicker than a 26 gauge has difficulty in making a bevel length 1.0 mm or less. Hence, it is preferable to use a needle tube thinner than the 26 gauge to set the protrusion length L of the needle tube 12 to a desired range (0.9 to 1.4 mm).

The needle protrusion surface 31a is formed such that a distance S from a periphery to a circumference surface of the needle tube 12 is 1.4 mm or less, and is preferably formed in a range of 0.3 to 1.4 mm. The distance S from the periphery of this needle protrusion surface 31a to the circumference surface of the needle tube 12 is set by taking into account that a pressure is applied to wheals formed when a drug is administered to the skin upper layer portion. That is, the needle protrusion surface 31a is set to a size which is sufficiently smaller than wheals formed at the skin upper layer portion and does not prevent formation of wheals. As a result, the needle protrusion surface 31a can press the skin around the needle tube 12 and prevent leakage of the administered drug.

The stable portion 36 is formed in a cylindrical shape protruding from the planar surface 24a of the connection piece 24 provided to the base portion 33. The needle tube 12 and the adjusting portion 31 are disposed in a cylindrical hole of the stable portion 36. That is, the stable portion 36 is formed in the cylindrical shape covering the surroundings of the adjusting portion 31 through which the needle tube 12 penetrates, and is formed apart from the needle tip 12a of the needle tube 12 in the radial direction.

As illustrated in FIG. 2, an end surface 36a of the stable portion 36 is positioned closer to the side of the proximal end 12b of the needle tube 12 than the needle protrusion surface 31a of the adjusting portion 31 is. When the needle tip 12a of the needle tube 12 punctures a biological body, the needle protrusion surface 31a first comes into contact with a skin surface and then comes into contact with the end surface 36a of the stable portion 36. In this case, the end surface 36a of the stable portion 36 comes into contact with the skin, so that it is possible to stabilize the drug injection device 1 and keep the needle tube 12 at a posture nearly vertical to the skin.

In this regard, even when the end surface 36a of the stable portion 36 is positioned on the same plane as the needle protrusion surface 31a or is positioned closer to the side of the needle tip 12a of the needle tube 12 than the needle protrusion surface 31a is, it is possible to keep the needle tube 12 at a posture nearly vertical to the skin. In this regard, when a bulge of the skin caused when the stable portion 36 is pressed against the skin is taken into account, a distance between the end surface 36a of the stable portion 36 and the needle protrusion surface 31a in the axial direction is preferably set to 1.3 mm or less.

Further, an inner diameter of the stable portion 36 is set to a value equal to or larger than the diameter of the wheals formed on the skin. More specifically, a distance T from an inner wall surface of the stable portion 36 to the periphery of the needle protrusion surface 31a is set to a range of 4 mm to 15 mm. Consequently, it is possible to prevent a pressure from being applied from the inner wall surface of the stable portion 36 to the wheals and thereby preventing formation of the wheals.

The shortest distance T from the inner wall surface of the stable portion 36 to an outer circumference surface of the adjusting portion 31 has no upper limit in particular as long as the shortest distance T is 4 mm or more. However, when the distance T is increased, an outer diameter of the stable portion 36 becomes large, and therefore, when the needle tube 12 punctures a thin arm like a child, it is difficult to place the entire end surface 36a of the stable portion 36 in contact with a skin. Hence, the distance T is preferably defined as 15 mm at maximum when thinness of children's arms is taken into account.

Further, when the distance S from the periphery of the needle protrusion surface 31a to the circumference surface of the needle tube 12 is 0.3 mm or more, the adjusting portion 31 does not enter a skin. Consequently, when the distance T (4 mm or more) from the inner wall surface of the stable portion 36 to the periphery of the needle protrusion surface 31a and the diameter (approximately 0.3 mm) of the needle protrusion surface 31a are taken into account, it is possible to set the inner diameter of the stable portion 36 to 9 mm or more.

In this regard, the shape of the stable portion 36 is not limited to a cylindrical shape, and may be, for example, a square tube shape such as a quadrangular prism and a hexagonal prism having a cylindrical hole at a center.

Further, the cap 50 is detachably fitted to the stable portion 36 (see FIG. 4). This cap 50 covers the needle tip 12a of the needle tube 12. Consequently, when the needle hub 13 is attached to the syringe 3, it is possible to prevent the needle tip 12a from contacting a fingertip of a user and the like. Further, it is possible to keep a safe state of the used drug injection device 1 or needle assembly 2 at all times, and the user can safely dispose the used drug injection device 1 or needle assembly 2.

The guide portion 32 is a distal end side portion of the second member 15 positioned closer to the outside of the radial direction than the stable portion 36 of the connection piece 24 is. This guide portion 32 includes a contact surface 32a that contacts the skin. The contact surface 32a is part of the planar surface 24a of the connection piece 24, and is a planar surface nearly parallel to the end surface 36a of the stable portion 36. By pressing the stable portion 36 until the contact surface 32a of the guide portion 32 contacts the skin, it is possible to secure a force of the stable portion 36 and the needle tube 12 for pressing the skin at a predetermined value or more at all times. Thus, the portion (corresponding to the protrusion length L) of the needle tube 12 protruding from the needle protrusion surface 31a reliably punctures the skin.

The length of a distance (referred to as a "guide portion height" below) Y from the contact surface 32a of the guide portion 32 to the end surface 36a of the stable portion 36 is set to enable the needle tube 12 and the stable portion 36 to press and puncture the skin by an appropriate force. In this regard, the appropriate pressing force of the needle tube 12 and the stable portion 36 is, for example, 3 to 20 N. As a result, the guide portion 32 guides for the user the pressing force of the needle tube 12 and the stable portion 36 to the skin, and it is possible to reliably position the needle tip 12a (blade surface) of the needle tube 12 at the skin upper layer portion and make the user feel safe.

The height Y of the guide portion 32 is optionally determined based on the inner diameter of the stable portion 36 and a length (referred to as "guide portion length" below) X from a distal end surface of the guide portion 32 to an outer circumference surface of the stable portion 36. When, for example, an inner diameter D of the stable portion 36 is 12 mm and the guide portion length X is 3.0 mm, the guide portion height Y is set to a range of 2.3 to 6.6 mm.

[Elastic Member]

Next, the elastic member 16 will be described. The elastic member 16 is disposed inside the cylindrical hole 26 which is the intermediate portion 19 of the first member 14, and is interposed between the first member 14 and the syringe 3. This elastic member 16 includes a deformation portion 40, a main body portion 41 and a flange portion 42 provided at one end of this main body portion 41 in the axial direction, and the deformation portion 40, the main body portion 41 and the flange portion 42 are integrally formed.

The main body portion 41 is formed in a nearly cylindrical shape, and the end surface 41a at a side opposite to a side at which the deformation portion 40 is formed comes into contact with the end surface 33b of the base portion 33 of the second member 15. Further, an outer diameter of the main body portion 41 is formed slightly larger than an inner diameter of an inner wall surface of the fitting portion 18 at the side of the insertion portion 20 provided to the first member 14. Thus, elasticity of the elastic member 16 allows the elastic member 16 to be retained in a liquid-tight manner at the side of the insertion portion 20 of the fitting portion 18.

The flange portion 42 is formed on an outer circumference surface of the main body portion 41 at the side of the end surface 41a, and is formed in a ring shape protruding from the outer circumference surface of the main body portion 41 in the radially outer direction. The flange portion 42 is formed larger than an inner diameter of the intermediate portion 19 which retains the main body portion 41, and smaller than an inner diameter of the insertion portion 20. Hence, one planar surface of the flange portion 42 comes into contact with the engagement portion 26a formed as a step shape between the intermediate portion 19 of the first member 14 and the insertion portion 20, and the other planar surface comes into contact with the end surface 33b of the base portion 33 of the second member 15. The engagement portion 26a of the first member 14 and the base portion 33 of the second member 15 sandwich the flange portion 42, so that the elastic member 16 is fixed to the needle hub 13.

The deformation portion 40 is composed of a cylindrical member provided at a side opposite to the side of the end surface 41a of the main body portion 41 which comes into contact with the base portion 33. An outer diameter of the deformation portion 40 is formed equally to or a little smaller than the outer diameter of the main body portion 41.

A side surface of the deformation portion 40 is formed continuing to a side surface of the main body portion 41, and an inner wall surface of the deformation portion 40 is formed continuing to an inner wall surface of the main body portion 41. Further, an end surface 40a of the deformation portion 40 at a side opposite to a side of the main body portion 41 is a contact surface which comes into contact with the distal end 6a of the drug ejection portion 6. During assembly of the drug injection device 1, the deformation portion 40 is pushed by the distal end 6a of the drug ejection portion 6 and is crushed toward the main body portion 41.

When using the drug injection device 1 according to the present embodiment, the user fits the drug ejection portion 6 to the fitting portion 18 to connect the syringe 3 and the needle assembly 2 and assemble the drug injection device 1. Hence, a fitting depth and strength of the drug ejection portion 6 with respect to the fitting portion 18 differ per user. Further, variations of dimensional tolerances of molded articles change a fitting depth of the drug ejection portion 6 with respect to the fitting portion 18. By contrast with this, the present embodiment employs a configuration where the deformation portion 40 deforms accompanying the distal end of the drug ejection portion 6, so that it is possible to provide an effect of reducing a dead volume produced by a difference in a fitting depth of the drug ejection portion 6 with respect to the fitting portion 18. In the present embodiment, the deformation portion 40 is formed, so that it is possible to reduce the dead volume produced by a difference in the fitting depth to 10 µL or less. In this regard, in the elastic member 16, the main body portion 41 also deforms more or less accompanying deformation of the deformation portion 40.

Hereinafter, a dimension of the elastic member 16 will be described with reference to FIG. 3. When a length A3 of the deformation portion 40 in the axial direction is 35% shorter than a length A1 of the entire elastic member 16 in the axial direction, a deformable width of the elastic member 16 in the axial direction becomes small, and a dead volume produced by a fitting depth difference varying per user is higher than 10 µL. Further, when the length A3 of the deformation portion 40 in the axial direction is 50% longer than the length A1 of the entire elastic member 16 in the axial direction, a deformation amount of the elastic member becomes large, and a liquid passing failure is highly likely to occur. Hence, the length A3 of the deformation portion 40 in the axial direction is preferably configured to be 35% or more and 50% or less with respect to the length A1 of the entire elastic member 16 in the axial direction.

Further, in the present embodiment, the elastic member 16 is provided with the insertion hole 43 through which the side of the proximal end 12b of the needle tube 12 protruding from the end surface 33b of the base portion 33 is inserted in the axial direction of the main body portion 41 and the deformation portion 40. An end surface side spaced portion 46, a contact surface side spaced portion 48 and a close contact portion 47 are formed on an inner wall surface of the insertion hole 43.

The end surface side spaced portion 46 includes the inner wall surface of the insertion hole 43 at the side of the main body portion 41, and forms an opening of the insertion hole 43 on the end surface 41a of the main body portion 41. This end surface side spaced portion 46 is spaced apart from an outer circumference surface of the needle tube 12, and is formed in such a tapered shape that the diameter of the insertion hole 43 becomes continuously larger toward the end surface 41a. Consequently, it is possible to easily insert the side of the proximal end 12b of the needle tube 12 protruding from the end surface 33b of the base portion 33 in the insertion hole 43. In this regard, the shape of the end surface side spaced portion 46 in the insertion hole 43 is not limited to the tapered shape as long as this tapered shape allows the needle tube 12 to be easily inserted in the insertion hole 43.

The contact surface side spaced portion 48 includes the inner wall surface of the insertion hole 43 at a side of the deformation portion 40, and forms the opening of the insertion hole 43 on the end surface 40a at the side of the deformation portion 40. This contact surface side spaced portion 48 is spaced apart from the outer circumference surface of the needle tube 12. Further, the inner wall surface forming the contact surface side spaced portion 48 is formed nearly parallel to the axial direction of the deformation portion 40. By providing the contact surface side spaced portion 48 to the elastic member 16, it is possible to prevent the deformation portion 40 from covering the proximal end 12b of the needle tube 12 and blocking the needle hole when the deformation portion 40 elastically deforms. In this regard, even when the contact surface side spaced portion 48 is provided, the deformation portion 40 is likely to block the proximal end 12b of the needle tube 12 during assembly of the drug injection device 1 depending on a protrusion length of the needle tube 12 toward the contact surface side spaced portion 48. The protrusion length of the needle tube 12 from the close contact portion 47 toward the deformation portion 40 to prevent this block will be described below.

The inner wall surface of the insertion hole 43 forming the contact surface side spaced portion 48 is formed nearly parallel to the axial direction of the deformation portion 40. However, the inner wall surface may be formed in such a tapered shape that the diameter of the insertion hole 43 continuously becomes larger from the close contact portion 47 toward an end surface of the deformation portion 40. That is, a shape of the contact surface side spaced portion 48 in the insertion hole 43 needs to be a shape which makes the deformation portion 40 hardly block the needle hole of the needle tube 12 when the deformation portion 40 elastically deforms.

The close contact portion 47 is formed between the end surface side spaced portion 46 and the contact surface side spaced portion 48, and is formed near a boundary between the main body portion 41 and the deformation portion 40. The close contact portion 47 is in close contact with the outer circumference surface of the needle tube 12 in a liquid-tight manner. Thus, it is possible to prevent a drug in the syringe 3 from infiltrating toward the second member 15 of the needle hub 13 from between the needle tube 12 and the elastic member 16.

A protrusion length A2 (see FIG. 3) of the needle tube 12 from the close contact portion 47 toward the contact surface side spaced portion 48 (toward the fitting portion 18) is set to such a length that, when the deformation portion 40 of the elastic member 16 is crushed against the distal end 6a of the drug ejection portion 6, the proximal end 12b of the needle tube 12 is exposed from the cylindrical hole 9 of the drug ejection portion 6 and does not damage the cylindrical hole 9 of the drug ejection portion 6. In this regard, the proximal end 12b of the needle tube 12 needs to be exposed toward the cylindrical hole 9 of the drug ejection portion 6 such that the deformation portion 40 does not completely block the needle hole, a liquid can pass and the user has no difficulty in administering the drug.

When the length A2 of the needle tube 12 protruding from the close contact portion 47 toward the fitting opening 18a is 45% shorter than the length A3 of the deformation portion 40 in the axial direction, and when the drug ejection portion 6 is fitted to the fitting portion 18, the deformation portion 40 crushed against the distal end 6a of the drug ejection portion 6 blocks the proximal end 12b of the needle tube 12 and thereby makes it impossible to eject the drug. Further, when the length A2 of the needle tube 12 protruding from the close contact portion 47 toward the fitting opening 18a is 245% longer than the length A3 of the deformation portion 40 in the axial direction, there is a concern that, for example, the drug ejection portion 6 is fitted to the fitting portion 18 obliquely with respect to the axial direction of the fitting portion 18, and the proximal end 12b of the needle tube 12 exposed in the cylindrical hole 9 of the drug ejection portion 6 damages the cylindrical hole 9 of the drug ejection portion 6. Consequently, in the present embodiment, the length A2 of the needle tube 12 protruding from the close contact portion 47 toward the fitting portion 18 is preferably set to a range of 45% or more and 245% or less with respect to the length A3 of the deformation portion 40 in the axial direction. Further, the length A2 is preferably 1.4 mm or more and 7.5 mm or less. Furthermore, the length A3 is preferably 2.5 mm or more and 3.1 mm or less.

Further, in the present embodiment, this elastic member 16 is provided, so that, when the syringe 3 and the needle assembly 2 are connected, the distal end 6a of the drug ejection portion 6 crushes the deformation portion 40 of the elastic member 16 and thereby the distal end 6a of the drug ejection portion 6 and the end surface of the deformation portion 40 of the elastic member 16 contact each other in a liquid-tight manner. Further, the needle tube 12 is exposed from a distal end of the crushed deformation portion 40 toward the drug ejection portion 6, so that the cylindrical hole 9 of the drug ejection portion 6 and the needle tube 12 continue to each other.

A material of the elastic member 16 may be any of various rubber materials such as natural rubber and silicone rubber, various thermoplastic elastomers such as polyurethane elastomers and styrene elastomers and elastic materials of mixture thereof.

The needle assembly 2 employing the above configuration is manufactured as follows. First, the needle tube 12 is inserted in the through-hole 25 of the base portion 33 of the second member 15. The adhesive is injected through the injection hole 35 formed in the base portion 33 in a state where the needle tip 12a of the needle tube 12 is protruded from the adjusting portion 31 by a defined length for puncturing a skin to adhere and fix the second member 15 and the needle tube 12. Next, the elastic member 16 is inserted in the intermediate portion 19 of the first member 14. Subsequently, the adhesive is applied on the guide portion 32 of the second member 15, and the base portion 33 of the second member 15 is inserted in the insertion portion 20 of the first member 14 to adhere and fix the fixing piece 34 of the first member 14 and the guide portion 32 of the second member 15. In this case, the needle assembly 2 is manufactured such that the length A2 of the needle tube 12 protruding from the close contact portion 47 toward the fitting portion 18 is preferably set to a range of 45% or more and 245% or less with respect to the length A3 of the deformation portion 40 in the axial direction. Thus, the needle assembly 2 is finished.

<2. Method for Assembling Drug Injection Device>

Figure 5:
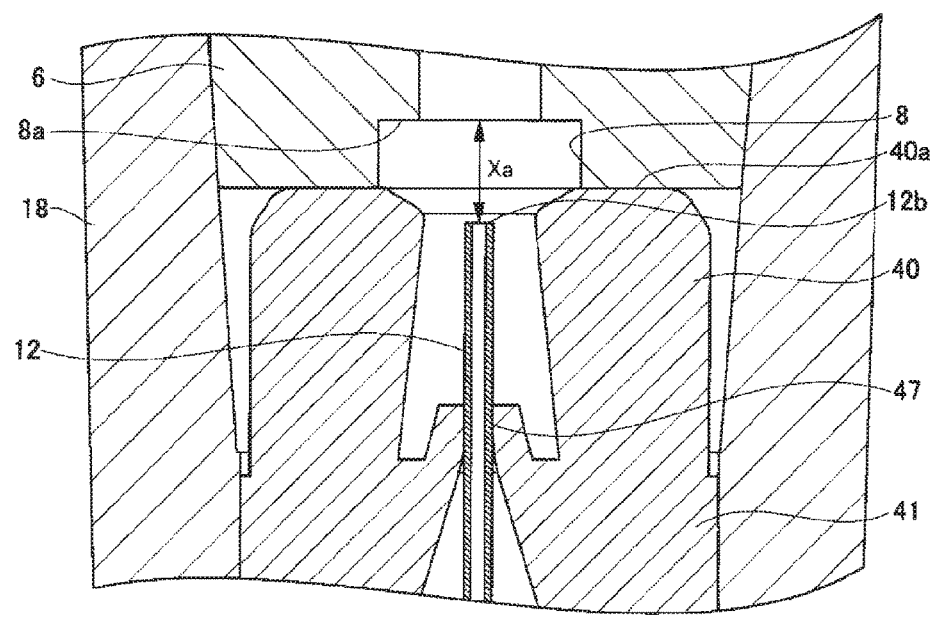
FIG. 5 is an enlarged view of main portions in FIG. 4.
Figure 6:
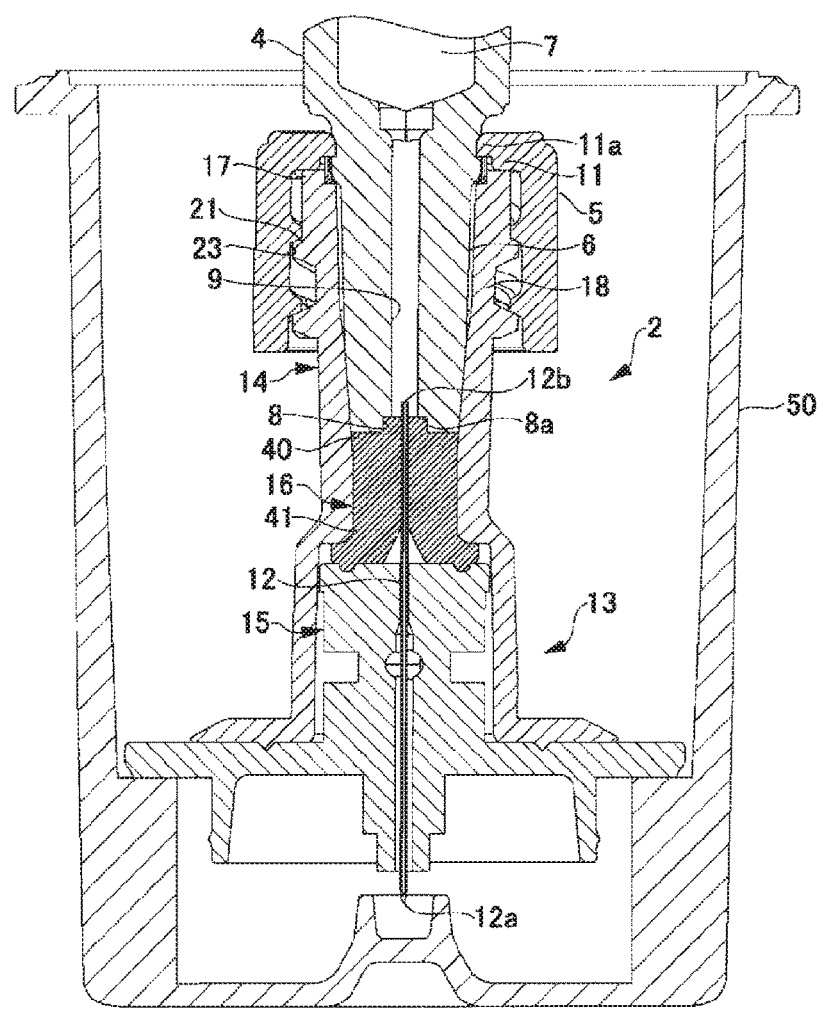
FIG. 6 is a view (part 2) illustrating how the drug ejection portion of the syringe is fitted to the needle assembly to assemble the drug injection device.
Figure 7:
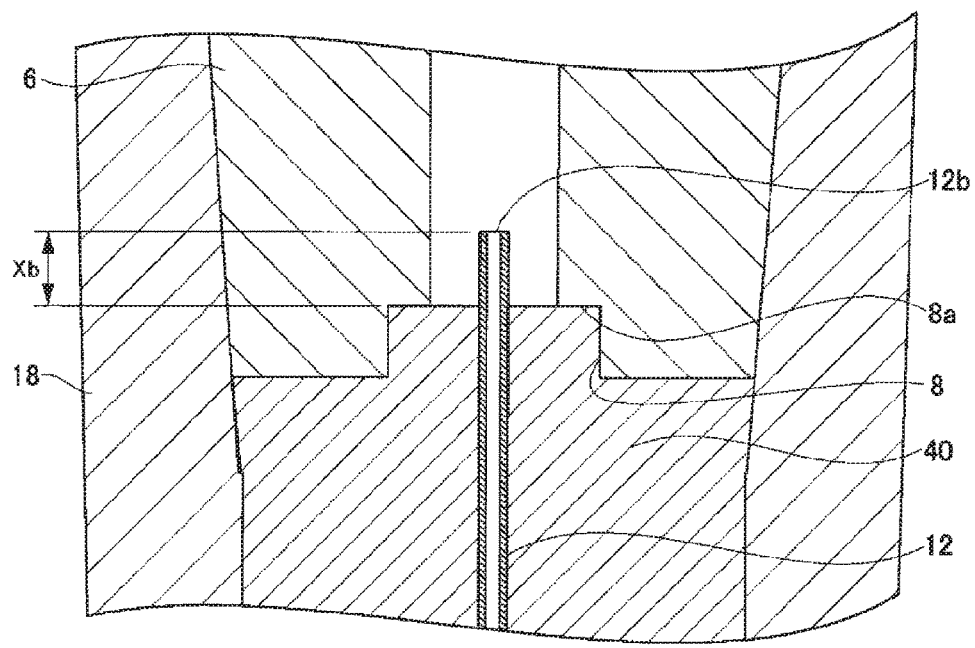
FIG. 7 is an enlarged view of main portions in FIG. 6.

Next, a method for connecting the needle assembly 2 to the drug ejection portion 6 and assembling the drug injection device 1 will be described. FIGS. 4 and 6 are views illustrating how the drug ejection portion 6 of the syringe 3 is fitted to the needle assembly 2 to assemble the drug injection device 1. FIG. 5 is an enlarged view of main portions in FIG. 4, and FIG. 7 is an enlarged view of main portions in FIG. 6.

As illustrated in FIG. 4, the drug ejection portion 6 of the syringe 3 is inserted in the fitting portion 18 of the needle assembly in a state where the needle assembly 2 is housed in the cap 50. The distal end of the drug ejection portion 6 is inserted in the cylindrical hole 18b through the fitting opening 18a of the fitting portion 18. In this case, an inner diameter of the guide wall 18d is formed larger than an outer diameter of the distal end 6a of the drug ejection portion 6, and therefore the distal end 6a of the drug ejection portion 6 is easily inserted in the fitting opening 18a.

The drug ejection portion 6 is further inserted in the cylindrical hole 18b. In this case, even when the drug ejection portion 6 inclines and the distal end 6a of the drug ejection portion 6 contacts the connection wall 18e, the connection wall 18e is obliquely formed in the tapered shape, so that the drug ejection portion 6 smoothly slides and moves along an inner wall of the cylindrical hole 18b. Consequently, it is possible to prevent the distal end 6a of the drug ejection portion 6 from being damaged.

The drug ejection portion 6 is inserted in the cylindrical hole 18b until the female screw portion 23 of the lock mechanism 5 contacts the male screw portion 21 of the fitting portion 18, and then the needle assembly 2 and the lock mechanism 5 are relatively turned to screw the male screw portion 21 and the female screw portion 23. In this case, the lock mechanism 5 is fixed to the syringe 3, so that, by rotating the syringe 3, the user can screw the male screw portion 21 and the female screw portion 23. Further, tightening this lock mechanism 5 in this way deeply inserts the drug ejection portion 6 in the cylindrical hole 18b of the fitting portion 18.

Thus, when the drug ejection portion 6 is inserted in the fitting portion 18, the drug ejection portion 6 contacts the fitting wall 18c of the fitting portion 18. A taper rate of the fitting wall 18c is set higher than the taper rate of the drug ejection portion 6, so that only the distal end outer rim of drug ejection portion 6 contacts the fitting wall 18c.

In this regard, FIG. 4 illustrates the state where the distal end 6a of the drug ejection portion 6 is fitted to the fitting wall 18c of the fitting portion 18 without applying a force much, and the syringe 3 is turned with respect to the needle assembly 2 at a connection torque of 0.05 N·m to screw the lock mechanism 5 and the fitting portion 18, and place the distal end 6a of the drug ejection portion 6 in contact with the deformation portion 40 of the elastic member 16. FIG. 5 is a view illustrating the enlarged deformation portion 40 in the state in FIG. 4. In the present embodiment, by setting the length of the needle tube 12 protruding from the close contact portion 47 toward the fitting portion 18 to the range of 45% or more and 245% or less with respect to the length of the deformation portion 40, it is possible to set a distance Xa from the close contact portion 47 to the end surface 8a of the expanded portion 8 of the drug ejection portion 6 in the axial direction to a predetermined range or less. A specific value of this distance Xa will be described in detail below. In this regard, the distance Xa from the end surface 8a of the expanded portion 8 in the axial direction to the needle tube 12 is defined based on the end surface 8a of the expanded portion 8 (zero) with a side in contact with the elastic member 16 as a positive direction and a side of the drug containing portion 7 as a negative direction. Hence, the distance Xa takes a plus value when the proximal end 12b of the needle tube 12 is closer to the elastic member 16 than the end surface 8a is as illustrated in FIG. 5, and takes a minus value when the proximal end 12b is closer to the drug containing portion 7.

As illustrated in FIG. 6, further tightening the lock mechanism 5 presses the distal end outer rim of the drug ejection portion 6 against the fitting wall 18c and further moves and deeply inserts the drug ejection portion 6 toward the elastic member 16. Further, at a point of time at which an end surface of the limiting portion 17 of the first member 14 comes into contact with the lock mechanism fixing portion 11 of the lock mechanism 5, the drug ejection portion 6 stops moving toward the elastic member 16. That is, the limiting portion 17 comes into contact with a bottom surface of the lock mechanism fixing portion 11, so that the drug ejection portion 6 is not pushed toward the elastic member 16 more.

The first member 14 is formed by using a synthetic resin. Hence, material characteristics of the first member 14 allow the fitting wall 18c to deform in a recessed shape when the drug ejection portion 6 is inserted in the fitting portion 18 until the end surface of the limiting portion 17 comes into contact with the bottom surface of the lock mechanism fixing portion 11. Thus, the distal end outer rim of the drug ejection portion 6 bites the fitting wall 18c. Thus, the distal end outer rim of the drug ejection portion 6 and the fitting wall 18c are placed in close contact, and the drug ejection portion 6 and the fitting wall 18c are fixed in a liquid-tight manner.

Further, when the drug ejection portion 6 is inserted in the fitting portion 18 until the end surface of the limiting portion 17 comes into contact with the bottom surface of the lock mechanism fixing portion 11, the deformation portion 40 of the elastic member 16 is crushed by the drug ejection portion 6 and bites the expanded portion 8 formed at the distal end of the drug ejection portion 6. Thus, the end surface 8a of the expanded portion 8 in the axial direction and the distal end 6a of the drug ejection portion 6, and the end surface of the deformation portion 40 of the elastic member 16 contact each other in a liquid-tight manner. In this case, by keeping a state where the needle tube 12 is exposed from a distal end of the crushed deformation portion 40 toward the drug ejection portion 6, the cylindrical hole 9 of the drug ejection portion 6 and the needle tube 12 continue to each other.

Further, when the drug ejection portion 6 is inserted in the fitting portion 18 until the end surface of the limiting portion 17 comes into contact with the bottom surface of the lock mechanism fixing portion 11, and the needle assembly 2 is locked in the drug ejection portion 6 by the lock mechanism 5, the assembly of the drug injection device 1 is finished.

FIG. 7 is a view illustrating the enlarged deformation portion 40 in the state in FIG. 6. In the present embodiment, by setting the length of the needle tube 12 protruding from the close contact portion 47 toward the fitting portion 18 to the range of 45% or more and 245% or less with respect to the length of the deformation portion 40, the proximal end 12b of the needle tube 12 protrudes from the close contact portion 47 toward the cylindrical hole 9 of the drug ejection portion 6 by a predetermined distance Xb when the assembly is finished. Consequently, it is possible to prevent the deformation portion 40 from blocking the proximal end 12b of the needle tube 12 and causing a liquid passing failure. In this regard, the distance Xb from the end surface 8a of the expanded portion 8 in the axial direction to the needle tube 12 is also defined based on the end surface 8a of the expanded portion 8 (zero) with the side in contact with the elastic member 16 as the positive direction and the side of the drug containing portion 7 as the negative direction.

Hence, the distance Xb takes a plus value when the proximal end 12b of the needle tube 12 is closer to the elastic member 16 than the end surface 8a is, and takes a minus value when the proximal end 12b is closer to the drug containing portion 7 as illustrated in FIG. 7. Xb is preferably 0 mm or more and 6.0 mm or less.

In this regard, an insertion depth of the drug ejection portion 6 in the fitting portion 18 differs by user. However, as long as the female screw portion 23 of the lock mechanism 5 and the male screw portion 21 of the fitting portion 18 are screwed together, the distal end 6a of the drug ejection portion 6 comes into contact with the deformation portion 40 of the elastic member 16 in a liquid-tight manner. That is, an insertion distance at which the drug ejection portion 6 is inserted in the fitting portion 18 until the limiting portion 17 comes into contact with the lock mechanism fixing portion 11 is a maximum insertion distance, and the drug ejection portion 6 may be locked at a position at which the limiting portion 17 does not come into contact with the lock mechanism fixing portion 11. In the present embodiment, when the limiting portion 17 comes into contact with the bottom surface of the lock mechanism fixing portion 11, the drug ejection portion 6 of the syringe 3 is not inserted in the fitting portion 18 more. Consequently, it is possible to prevent the fitting claws 11a from being damaged when a pushing force of the drug ejection portion 6 in the fitting portion 18 exceeds a fitting force of the fitting claws 11a and the recessed portion 6b of the drug ejection portion 6, and prevent the lock mechanism 5 from being detached from the drug ejection portion 6.

In the present embodiment, the distal end outer rim of the drug ejection portion 6 is formed in a small circular shape, and, when the drug ejection portion 6 is fitted in the fitting portion 18, this small distal end outer rim is pressed against the fitting wall 18c. Further, the taper rate of the male tapered shape of the drug ejection portion 6 is formed lower than the taper rate of the female tapered shape of the fitting portion 18. As a result, a pressure at which the drug ejection portion 6 is pressed against the fitting wall 18c entirely concentrates on a narrow area of the fitting wall 18c which the distal end outer rim of the drug ejection portion 6 contacts. That is, a gap is made more or less between the fitting wall 18c and the side surface of the drug ejection portion 6, and therefore a force concentrates on the distal end outer rim of the drug ejection portion 6.

Hence, even a weak force which presses the needle assembly 2 and the drug ejection portion 6 can easily deform the fitting wall 18c and make the distal end outer rim of the drug ejection portion 6 easily bite the fitting wall 18c. Consequently, it is possible to fit the needle assembly 2 and the drug ejection portion 6 quickly in a liquid-tight manner, and reliably prevent leakage of a liquid.

When the needle assembly 2 and the drug ejection portion 6 have the tapered shape of the same taper rate in the drug injection device 1, a pressure needs to be applied such that the fitting wall 18c of the needle assembly 2 and the side surface of the drug ejection portion 6 rub against each other, and a friction resistance becomes high. Hence, a relatively large force is necessary to assemble the needle assembly 2 and the syringe 3. By contrast with this, in the present embodiment, by forming the taper rate of the male tapered shape of the drug ejection portion 6 smaller than the taper rate of the female tapered shape of the fitting portion 18, even a weak force can reliably fit the needle assembly 2 and the drug ejection portion 6.

The material of the first member 14 is not limited to a relatively soft material like polypropylene, and a relatively hard material such as polycarbonate and cyclo-olefin polymer can be used as long as the material can make the distal end outer rim of the drug ejection portion 6 sufficiently bite the fitting wall 18c.

A value of M of the taper rate of the fitting wall 18c needs to be optionally determined as a value higher than N. However, when the value of M is not different from N so much, a biting amount that the distal end outer rim of the drug ejection portion 6 bites the fitting wall 18c becomes small. Therefore, the value of M is preferably $M \geq 1.5$ N ($M \geq 9$ in case of N=6) and is more preferably $M \geq 2$ N ($M \geq 12$ in case of N=6). When the value of M is by far larger than N, the diameter of the cylindrical hole becomes large. Hence, taking an actual range into account based on a relationship between a wall thickness and an outer diameter of the fitting portion 18, the value of M is preferably $M \leq 10$ N ($M \leq 30$ in case of N=6), is more preferably $M \leq 5$ N ($M \leq 30$ in case of N=6), and is still more preferably $M \leq 3$ N (N=6 and $M \leq 18$). An example of a range is that the value of M is preferably in a range of M=1.5 N to 10 N (M=9 to 60 in case of N=6), is more preferably in a range of M=2 N to 5 N (M=12 to 30 in case of N=6) and is still more preferably in a range of M=2 N to 3 N (M=12 to 18 in case of N=6).

Further, in the present embodiment, when the drug injection device 1 is assembled, a protrusion length of the needle tube 12 from the close contact portion 47 toward the contact surface side spaced portion 48 is set to such a length that, when the deformation portion 40 of the elastic member 16 is crushed against the distal end 6a of the drug ejection portion 6, the proximal end 12b of the needle tube 12 is exposed from the cylindrical hole 9 of the drug ejection portion 6 without being blocked and does not damage the cylindrical hole 9 of the drug ejection portion 6. Consequently, it is possible to prevent a liquid passing failure.

In this regard, an experiment was conducted to check a liquid passing state when the protrusion length of the needle tube 12 from the close contact portion 47 toward the contact surface side spaced portion 48 (toward the fitting opening 18a) was changed. In this experiment, the liquid passing state was checked in case where a distance from the end surface 8a of the expanded portion 8 in the axial direction to the proximal end 12b of the needle tube 12 when the drug injection device 1 was assembled was changed to 0.9 mm to 1.5 mm. The distance from the end surface 8a of the expanded portion 8 in the axial direction to the proximal end 12b of the needle tube 12 is the distance Xa in the states illustrated in FIGS. 4 and 5. That is, the distance Xa from the proximal end 12b of the needle tube 12 to the end surface 8a of the expanded portion 8 in case where the drug ejection portion 6 was fitted and connected to the fitting portion 18 without applying a force much was changed to test a change in the liquid passing state. The distance Xa was changed by changing the protrusion length of the needle tube 12 from the close contact portion 47. In this regard, a contact position of the drug ejection portion 6 which contacts the elastic member 16 illustrated in FIGS. 4 and 5 is a reference contact position.

Further, in the drug injection device 1 used in the experiment, the depth of the drug ejection portion 6 in the axial direction of the expanded portion 8 was 0.4 to 0.6 mm, the length of the elastic member 16 in the axial direction was 6.5 mm to 6.8 mm, the outer diameter of the deformation portion 40 was 3.3 mm to 3.5 mm, the length of the deformation portion 40 in the axial direction was 2.9 mm to 3.1 mm and the thickness of the deformation portion 40 in the radial direction was in a range of 0.9 mm or more and 1.1 mm or less.

In the experiment, the user assembled drug injection devices whose distances Xa were set to 0.9 mm to 1.5 mm by applying a higher force than an average force during assembly. More specifically, the user pushed and fitted the drug ejection portion 6 toward the fitting portion 18 by a load of 25 N and rotated the syringe 3 at a connection torque of 0.26 N·m to screw the lock mechanism 5 to the fitting portion 18 and connect the syringe 3 and the needle assembly 2.

Further, a peak load when a drug was ejected at a speed of 100 mm/min from the drug injection device according to an experiment example assembled as described was measured. In this regard, assuming that this peak load was greater than a peak load in case where a drug was ejected from the drug injection device in a normal state where a liquid passing failure did not occur, and the liquid passing failure was determined when a difference between these peak loads was larger than 15 N, a rate that the liquid passing failure occurred was tested. This determination criterion was set based on a sensory test result obtained when the user felt heavier than usual to administer a drug by pressing a plunger. Following table 1 illustrates the experiment result of the drug injection device according to this experiment result.

TABLE 1

| Distance Xa/mm | Experiment result | Determination |
|---|---|---|
| 1.5 | 20% | X |
| 1.3 | 13% | X |
| 1.2 | 5% | X |
| 1.1 | 2% | X |
| 1.0 | 0% | ○ |
| 0.9 | 0% | ○ |

Table 1 shows that, when the distance Xa between the proximal end 12b of the needle tube 12 and the end surface 8a of the expanded portion 8 was 1.0 mm or less, the liquid passing failure did not occur. Hence, when a specific value of the distance from the end surface 8a of the expanded portion 8 to the proximal end 12b of the needle tube 12 in a state where the drug ejection portion 6 and the elastic member 16 are in the reference contact state is 1.0 mm or less, it is possible to prevent a liquid passing failure. Further, from a viewpoint that the needle tube 12 does not damage the cylindrical hole 9 of the drug ejection portion 6 during assembly of the drug injection device 1, and when the drug ejection portion 6 and the elastic member 16 are at the reference contact position, the distance Xa from the end surface 8a of the expanded portion 8 in the axial direction to the needle tube 12 is preferably −5.3 mm or more. That is, a preferable range of the distance Xa is −5.3 mm or more and 1.0 mm or less. In this regard, the distance from the end surface 8a of the expanded portion 8 in the axial direction to the needle tube 12 was defined based on the end surface 8a of the expanded portion 8 (zero) with the side in contact with the elastic member 16 as the positive direction and the side of the fitting portion 18 as the negative direction.

As described above, by setting the length of the needle tube 12 protruding from the close contact portion 47 toward the fitting opening to the range of 45% or more and 245% or less with respect to the deformation portion 40, the drug injection device 1 according to the present embodiment can prevent a liquid passing failure. By setting the distance Xa between the proximal end 12b of the needle tube 12 and the end surface 8a of the expanded portion 8 to 1.0 mm or less in terms of a more realistic value based on an actual design of the drug injection device 1, it is possible to prevent the liquid passing failure. Thus, even when the user strongly pushes the drug ejection portion 6 to the fitting portion 18 at a high speed and connects the drug ejection portion 6 to the fitting portion 18 during assembly of the drug injection device 1, the deformation portion 40 does not block the proximal end 12b of the needle tube 12 and it is possible to prevent the liquid passing failure.

The embodiment of the drug injection device and the needle assembly according to the present invention has been described above. However, the present invention is not limited to the above embodiment, and can be variously modified and carried out without departing from the scope of the invention recited in the claims.

In the above embodiment, the taper rate of the drug ejection portion is, for example, N=6 yet may be optionally changed. Further, the above embodiment employs a configuration where the taper rate of the drug ejection portion and the taper rate of the fitting portion are different. However, it is possible to provide the effect of the present invention even when the taper rates are the same.

Further, the above embodiment employs a configuration including the lock mechanism 5 composed of a different member from that of the drug ejection portion 6. However, the present invention may employ a configuration where the lock mechanism is provided to the drug ejection portion 6. In this case, by forming the male screw portion on the outer circumference surface of the drug ejection portion 6 and forming on the inner circumference surface of the fitting portion 18 the female screw portion screwed to the male screw portion formed in the drug ejection portion 6, it is possible to fix the drug ejection portion 6 to the fitting portion 18.

REFERENCE SIGNS LIST

1 . . . Drug injection device,
2 . . . Needle assembly,
3 . . . Syringe,
4 . . . Syringe main body,
5 . . . Lock mechanism,
6 . . . Drug ejection portion,
7 . . . Drug containing portion,
8 . . . Expanded portion,
10 . . . Lock main body portion,
11 . . . Lock mechanism fixing portion,
11a . . . Fitting claw,
12 . . . Needle tube,
12a . . . Needle tip,
12b . . . Proximal end,
13 . . . Needle hub,
14 . . . First member,
15 . . . Second member,
16 . . . Elastic member,
17 . . . Limiting portion,
18 . . . Fitting portion,
19 . . . Intermediate portion,
20 . . . Insertion portion,
21 . . . Male screw portion,
23 . . . Female screw portion,
24 . . . Connection piece,
25 . . . Through-hole,
30 . . . Skin contact portion,
31 . . . Adjusting portion,
32 . . . Guide portion,
33 . . . Base portion,
34 . . . Fixing piece, 35 . . . Injection hole,
36 . . . Stable portion,
40 . . . Deformation portion,
41 . . . Main body portion,
42 . . . Flange portion,
43 . . . Insertion hole,
46 . . . End surface side spaced portion,
47 . . . Close contact portion,
48 . . . Contact surface side spaced portion

The invention claimed is:

1. A needle assembly configured to be connected to a drug container that includes a drug ejection portion having a male tapered shape with an outer diameter that becomes smaller toward a distal end, the needle assembly comprising:
   a needle tube that includes, at a distal end, a needle tip configured to puncture skin;
   a fitting portion having a fitting opening in which the drug ejection portion of the drug container is insertable, the fitting portion having a female tapered shape;
   an intermediate portion located distal of the fitting portion;
   a retaining portion that retains the needle tube; and
   an elastic member comprising:
      a main body portion located in the intermediate portion, wherein an outer diameter of the main body portion before insertion in the intermediate portion is larger than an inner diameter of an inner wall surface of the intermediate portion, such that the main body portion is contacted by the inner wall surface and retained in the intermediate portion in a liquid-tight manner,
      a contact portion that contacts the needle tube such that a proximal portion of the needle tube protrudes from the contact portion toward the fitting opening, and
      a deformation portion that extends from the contact portion toward the fitting opening and is configured to deform when the drug ejection portion of the drug container comes into contact with the elastic member,
   wherein a length of the deformation portion is in a range of 35% or more and 50% or less with respect to a length of the elastic member, and
   wherein a length of a portion of the needle tube that protrudes from the close contact portion toward the fitting portion is in a range of 45% or more and 245% or less with respect to the length of the deformation portion.

2. The needle assembly according to claim 1, wherein an outer diameter of the deformation portion is in a range of 3.3 mm or more and 3.5 mm or less, and a thickness of a wall of the deformation portion in a radial direction is in a range of 0.9 mm or more and 1.1 mm or less.

3. A drug injection device comprising:
   a drug container that includes a drug ejection portion having a male tapered shape with an outer diameter that becomes smaller toward a distal end; and
   a needle assembly configured to be connected to the drug container, the needle assembly comprising:
      a needle tube that includes, at a distal end, a needle tip configured to puncture skin;
      a fitting portion having a fitting opening in which the drug ejection portion of the drug container is insertable, the fitting portion having a female tapered shape;
      an intermediate portion located distal of the fitting portion;
      a retaining portion that retains the needle tube; and
      an elastic member comprising:
         a main body portion located in the intermediate portion, wherein an outer diameter of the main body portion before insertion in the intermediate portion is larger than an inner diameter of an inner wall surface of the intermediate portion, such that the main body portion is contacted by the inner wall surface and retained in the intermediate portion in a liquid-tight manner,
         a contact portion that contacts and retains the needle tube such that a proximal portion of the needle tube protrudes from the contact portion toward the fitting opening, and
         a deformation portion that extends from the contact portion toward the fitting opening and is configured to deform when the drug ejection portion of the drug container comes into contact with the elastic member,
      wherein a length of the deformation portion is in a range of 35% or more and 50% or less with respect to a length of the elastic member, and
      wherein a length of a portion of the needle tube that protrudes from the close contact portion toward the fitting portion is in a range of 45% or more and 245% or less with respect to the length of the deformation portion.

4. The drug injection device according to claim 3, wherein an outer diameter of the deformation portion is in a range of 3.3 mm or more and 3.5 mm or less, and a thickness of a wall of the deformation portion in a radial direction is in a range of 0.9 mm or more and 1.1 mm or less.

5. The drug injection device according to claim 4, wherein:
   wherein the drug ejection portion has a cylindrical hole having a first portion with a first diameter, and a second, expanded portion located at a distal end side of the cylindrical hole, the second, expanded portion having a second diameter that is larger than the first diameter,
   a depth of the expanded portion in an axial direction is 0.4 mm or more and 0.6 mm or less, and
   when the drug ejection portion is fitted to the fitting portion and the distal end of the drug ejecting portion comes into contact with the deformation portion of the elastic member, a length from an end surface of the expanded portion to a proximal end of the needle tube in the axial direction is 1.0 mm or less.

6. The drug injection device according to claim 3, wherein a taper rate of the female tapered shape of the fitting portion is greater than a taper rate of the male tapered shape of the drug ejection portion.

7. The drug injection device according to claim 4, wherein a taper rate of the female tapered shape of the fitting portion is greater than a taper rate of the male tapered shape of the drug ejection portion.

8. The drug injection device according to claim 5, wherein a taper rate of the female tapered shape of the fitting portion is greater than a taper rate of the male tapered shape of the drug ejection portion.

* * * * *